(12) United States Patent
Gonzales

(10) Patent No.: US 9,492,573 B2
(45) Date of Patent: Nov. 15, 2016

(54) METHOD OF TREATING CHOLANGIOCARCINOMA AND APPARATUS

(75) Inventor: Gilbert R. Gonzales, Tucson, AZ (US)

(73) Assignee: Serene, LLC, The Woodlands, TX (US)

(*) Notice: Subject to any disclaimer, the term of this patent is extended or adjusted under 35 U.S.C. 154(b) by 0 days.

(21) Appl. No.: 13/541,823

(22) Filed: Jul. 5, 2012

(65) Prior Publication Data

US 2013/0012756 A1 Jan. 10, 2013

Related U.S. Application Data

(60) Provisional application No. 61/504,807, filed on Jul. 6, 2011.

(51) Int. Cl.
*A61N 5/10* (2006.01)
*A61K 51/12* (2006.01)

(52) U.S. Cl.
CPC .......... *A61K 51/1282* (2013.01); *A61N 5/1002* (2013.01); *A61N 2005/1025* (2013.01)

(58) Field of Classification Search
CPC ..... A61F 2/04; A61F 2002/041; A61N 5/10; A61N 5/1001; A61N 5/1002; A61N 2005/1019; A61N 2005/1025; A61K 51/1282
USPC ...................................... 600/1, 3; 623/23.65
See application file for complete search history.

(56) References Cited

U.S. PATENT DOCUMENTS

| 5,118,394 | A | 6/1992 | Makino et al. | |
|---|---|---|---|---|
| 6,383,217 | B1 | 5/2002 | Satz | |
| 7,182,745 | B2* | 2/2007 | Desmond, III | 604/8 |
| 7,972,261 | B2 | 7/2011 | Lamoureux et al. | |
| 2004/0237282 | A1 | 12/2004 | Hines | |
| 2006/0157891 | A1* | 7/2006 | Hardy et al. | 264/261 |
| 2006/0229711 | A1* | 10/2006 | Yan | A61F 2/02 623/1.38 |
| 2006/0235504 | A1 | 10/2006 | Gonzales | |
| 2007/0038292 | A1* | 2/2007 | Danielpour | 623/1.42 |
| 2010/0137673 | A1* | 6/2010 | Srivastava et al. | 600/3 |
| 2010/0137970 | A1 | 6/2010 | Srivastava et al. | |

FOREIGN PATENT DOCUMENTS

| WO | 00/28554 | 5/2000 |
|---|---|---|
| WO | WO 0028554 A1 * | 5/2000 |

OTHER PUBLICATIONS

JEDEC Standard, Measuring Whisker Growth on Tin and Tin Alloy Surface Finishes, JESD22A121, JEDEC Solid State Technology Association, May 2005.
Amélie Monami; International Search Report and Written Opinion issued in International Patent Application No. PCT/US2012/045693; Oct. 8, 2012; 12 pages; European Patent Office.
He Gui-Jin et al.; Induction of Biliary Cholangiocarcinoma Celll Apoptosis by 103Pd Cholangial Radioactive Stent y-rays; Sep. 30, 2007; pp. 1020-1024; Chin Med J.
Je Hwan Won, MD., et al.; Effects of a Holmium-166 Incorporated Covered Stent Placement in Normal Canine Common Bile Ducts; May 2005; pp. 705-711.
International Search Report on Patentability from the International Bureau of WIPO issued in corresponding PCT Application No. PCT/US2012/045693, dated Jan. 7, 2014 (8 pages).

* cited by examiner

*Primary Examiner* — Charles A Marmor, II
*Assistant Examiner* — Thaddeus Cox
(74) *Attorney, Agent, or Firm* — Wood Herron & Evans LLP

(57) ABSTRACT

Biological implants have an electroplated surface wherein a substantial portion of the electroplated surface is covered with dendrites. The dendrites assist in maintaining the implant in location. When the metal is a radioactive metal or the surface of the electroplated is coated with a radioactive material, the dendrites increase surface area thereby increasing radiation dosage and further extend the radioactive surface farther away from the surface of the implant, further enhancing radioactive emission. This is particularly useful for a cholangiocarcinoma stent which can be implanted into the biliary stent to treat cholangiocarcinoma.

12 Claims, 2 Drawing Sheets

METHOD OF TREATING CHOLANGIOCARCINOMA AND APPARATUS

RELATED APPLICATION

This application is related to and claims the benefit of U.S. Provisional Patent Application Ser. No. 61/504,807, filed on Jul. 6, 2011, the disclosure of which is incorporated herein by reference.

BACKGROUND OF THE INVENTION

Biliary, pancreatic and hilar ducts may become occluded when biliary, pancreatic, or hepatic cancer invades the duct or an external cancer mass compresses and blocks the ducts. Cholangiocarcinomas are malignancies of the biliary duct system that start in the liver or extra-hepatic biliary ducts. They can start in one of the ducts and invade and extend to the ampulla of Vater.

These malignancies have a very high morbidity and mortality rate. As an example, pancreatic cancer patients have a life span that is measured in months after diagnosis, often after extensive invasive treatments and chemotherapy. This high mortality is due to the rapid progression of the cancer resulting in complications that are often the cause of the patient's demise. The complications of pancreatic cancer include ductal occlusion with biliary flow obstructions resulting in jaundice and encephalopathy, ascending cholangitis and rapid death from sepsis, very severe pain that is difficult to control, even with high dose opioids that results in medication-induced sedation, cachexia and wasting, and many other complications.

The issues that occur in ductal obstruction and occlusion are unique to the biliary system due to the "harsh environment" of the biliary drainage system as pancreatic and biliary enzymes and the "dirty environment" with the fungi and bacteria that inhabit the ducts make stasis and injury to these ducts susceptible to complete occlusion by biofilm (bacteria) and organic masses ('fungal balls'). In addition, bleeding of the ducts, with or without stent placement can cause clot formation and occlusion. Invasion by the tumor within the ductal wall and occlusion of the duct by external compression by a tumor mass are also common causes of complications.

Treatment of ductal occlusion has been partially addressed with stainless steel stents, cobalt chromium stents, inexpensive plastic stents and, more recently, shape memory alloy stents. These stents are placed in a harsh enzymatic environment and re-occlusion occurs frequently. If the patient survives a month or months, a stent-in-stent can be performed but often times the complications described above result in the terminal state before this can be performed.

One problem with many different types of implants, and, in particular, biliary stents, is migration of the implant or stent from the desired location. Once the stent migrates, the bile duct closes. This, of course, can be a problem with other stents, as well as implants of various sizes and shapes.

Frequently, it is desirable to place a tubular implant, such as a stent, at the point at which the biliary duct enters the duodenum. This particular opening widens as the biliary duct approaches the duodenum. As a result, the desired shape of an implant would be frustoconical, but such an implant inherently tends to migrate.

SUMMARY OF THE INVENTION

The present invention is premised on the realization that the movement of an implant, such as a stent, is reduced by providing an implant that has an exterior surface with dendrite formation. Such a stent is formed by electroplating the exterior surface of the implant with a biologically compatible metal such as tin, or the like, under conditions that promote dendrite formation. The dendrites are tree-like or fern-like crystalline structures that rise from the plated surface up to about 100 to 150 microns and, in effect, roughen the exterior surface of the implant. When implants covered in dendrites are employed, the dendrites engage the adjacent tissue, inhibiting movement of the implant. In particular, this invention incorporates this feature into a biliary stent or implant which due to the roughened exterior surface is less likely to migrate.

In one embodiment of the present invention, the implant emits radiation effective to treat the cancer. In particular, the exterior surface can incorporate tin-117 m, which is a CEES emitter. The roughened surface not only deters migration, but, in addition allows the radiation to migrate more irregularly and farther from the surface of the stent than would be emitted with a smooth surface. Further, an implant electroplated with a non-radioactive metal can be coated with a radioactive material such as phosphorous 32 to provide similar benefits.

The objects and advantages of the present invention will be further appreciated in light of the following detailed description and drawings in which:

DETAILED DESCRIPTION

Figure 1:
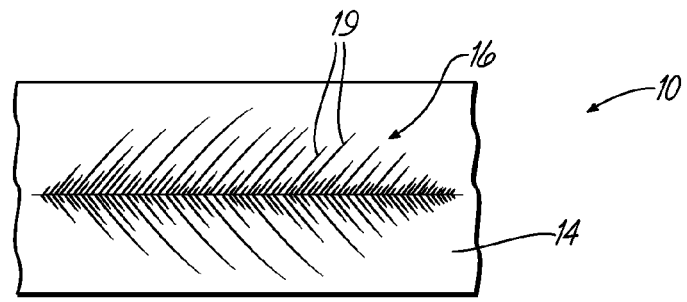
FIG. 1 is a diagrammatic view of an enlarged section of an implant.
Figure 2:
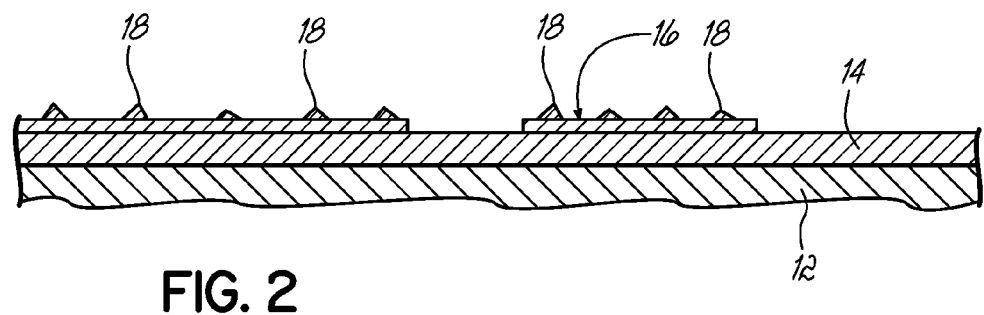
FIG. 2 is a diagrammatical cross-sectional view of the implant.

The present invention is an implant 10 such as a stent, or the like, which has an exterior surface 12 electroplated with a metal layer 14, and significantly covered with the dendrites 16. Dendrites 16 are irregular tree-shaped crystalline growths on the surface of certain metals. They extend from the surface out 100 to 150 microns. The dendrites include low sharp protrusions or hillocks 18. The individual "hairs" 19 appear as irregularities similar to a slipped tectonic plate. In most electroplating applications, dendrites are undesirable and dendrite growth is inhibited.

The implant can be a wide variety of different implants such as expandable stents and tubes. The implant can emit radiation for therapeutic or imaging purposes, or can be non-radioactive.

As indicated, the exterior surface 12 of the implant is electroplated metal layer 14. A portion of the layer 14 will be coated with dendrites 16, generally greater than about 1.5% and preferably at least 2%. The surface can be coated with 2% dendrites, 3% dendrites, 12% dendrites, 15% dendrites, or more. These percentages are by area. It is preferable to have a larger percentage of the surface coated with dendrites. But, this can vary widely based on the implant, whether it is solid or mesh, as well as the malady being treated, and the metal.

As indicated, the implant can be any implant which can be electroplated with a metal. Generally, the implant itself will be formed from a biologically acceptable metal such as stainless steel, nitinol, cobalt chromium, titanium, and the like. In turn, the exterior surface of the implant will be electroplated, again with a biologically acceptable metal. One such metal is tin, other such metals could include nickel, silver, gold, titanium, and the like. The implant is formed from the biologically acceptable metal using well-known techniques. Once formed, the implant is electroplated with the second biologically acceptable metal which can be the same or different from the metal used to form the implant.

Generally, when electroplating a surface, one attempts to prevent formation of dendrites. But, in the present invention dendrite growth is promoted, primarily by not taking the steps required to inhibit growth. For example, certain chemicals can be added to the electrolytic bath to inhibit dendrite formation, for example, gelatin or other proteins. These preferably would not be included or would be minimized in the electrolyte solution. Further, to avoid dendrite formation, it is preferred to conduct the electrolysis with a static, non-agitated electrolyte solution. Accordingly, agitating the solution during formation will increase dendrite formation. Rapid and irregular bubbling of inert gases or hydrogen will also promote dendrite formation. Variation of the current applied to the electrocoating bath also promotes dendrite formation. The electroplated implant should not be annealed or heat treated as this can reduce the dendrite coverage.

In certain embodiments, the implant will be radioactive. The exterior surface can be electroplated with a radioactive metal such as tin-117 m. When tin-117 m is electroplated onto a surface, additional cold tin may be added to the electrolyte solution as a relatively minor amount of the radioactive tin is used to coat the exterior surface. Thus, the electroplated surface will be tin-117 m optionally combined with cold tin.

Figure 3:
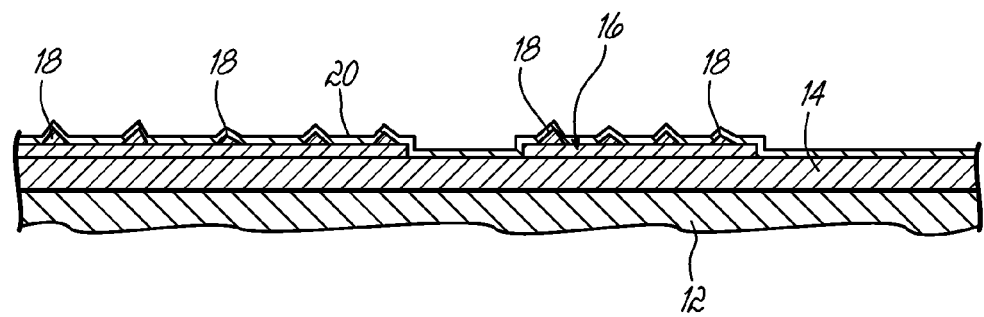
FIG. 3 is a diagrammatical cross-sectional view of an alternate embodiment of the present invention.

As shown in FIG. 3, the exterior surface 12 of the implant 10 can be electroplated with a nonradioactive biologically acceptable layer 14 of metal such as cold tin to form the dendrites 16. The metal layer 14 can include a coating layer 20. Layer 20 can be a radioactive material such as phosphorus-32. Other radioactive compounds suitable for use in the present invention include rhenium-188, nickel-63, palladium-103, iron-59, as well as radioactive silver-gallium alloys.

When coating an implant with tin-117 m, dendrites are produced by residual stresses (i.e., stresses that remain after the original electroplating) during the electroplating process. One process is described below.

For example, a stainless steel stent can be at least partially coated (i.e., external surface only) with Sn-117 m wherein the Sn-117 m is partially in the form of dendrites on a surface of the stent. The stent may be coated with Sn-117 m on the outer surface of the stent struts with the inner stent surface uncoated or less coated to allow for treatment of the ductal wall neoplasm (i.e., the area against the outer strut surface) while allowing the inner surface of the stent struts to re-endothelialize.

A 316 L stainless steel 5 to 10 French, 1.8 cm to 15 cm in length stent is typical. The stent may have a strut design similar to an ACS MultiLink™ stent. The stent is first thoroughly rinsed by acetone or ethyl alcohol (with sonication, if needed) to remove adventitious grease and dust particles. A pair of tweezers is inserted into the stent prior to electroplating so that $^{117m}$Sn activity is restricted to the outside surfaces of the wire to prevent substantial irradiation of the lumen. (See U.S. Published Application No. 2010/0137673 A1, the disclosure of which is incorporated herein by reference.)

Then, the stent is submerged in the activation and plating solution comprising either 0.5 M $CoCl_2$ and 1 M Cl or 0.1-0.2 M $NiCl_2$ and 2M HCl, at a current density of 5-10 $mA/cm^2$, for about 1-3 min. Hydrochloric acid activates stents by dissolving the passive film on stainless steel and the metal ion $Co^{2+}$ or $Ni^{2+}$ nucleates on steel to generate a "seed" layer and provide better bonding of Sn to steel. Cobalt or nickel deposition is followed by a quick rinsing with water and transferring to an Sn plating solution, to which the potential is quickly applied to avoid significant dissolution of Co or Ni.

To prepare the plating solution from the radioactive stannic tin, a weighted piece of high purity cold tin wire is placed in a dissolution vessel along with an aliquot of radioactive tin and 12 M hydrochloric acid to establish an equilibrium such that the radioactive tin behaves like the "cold" tin (both as $Sn^{2+}$). (See U.S. Published Application No. 2010/037970 A1, the disclosure of which is incorporated herein by reference.)

The quality of the Sn coating is checked by standard tests for bonding and adhesion using scotch tape and bending the wire constituting the stent at 90 degrees. If the deposit does not peel off with the tape, or no cracks occur upon bending, the adhesion can be considered satisfactory.

The Sn plating solution comprises either $(1-8)\times10^{-3}$ M $Sn^{2+}$, 0.2 M $H_2SO_4$, 0.1 M HCl and 2 g/l of resorcinol or $1\times10^{-2}$ M $Sn^{2+}$, 2 M $H_xSO_4$, and 2 gl/l of gelatin. The electroplating is carried out at room temperature with either potentiostatic or galvanostatic deposition at the potential E=0.5 to –055V vs. Ag/AbCl/Cl⁻ reference electrode and the current density is 0.1-0.5 $mA/cm^2$. In addition, $10^{-7}$-$10^{-2}$ M Tl is added to the plating solution to reduce the rate of $H_2$ evolution, which decreases the quality of Sn coating.

With or without a seed layer, argon or $N_2$ bubbling may be used to enhance mass transport and help compensate for the adverse effects or low $Sn^{2+}$ concentration of the electroplating solution on the quality of the Sn coating by allowing greater adhesion and smoothness. This method produces an electroplated tin layer with substantial dendrite formation.

Figure 4:
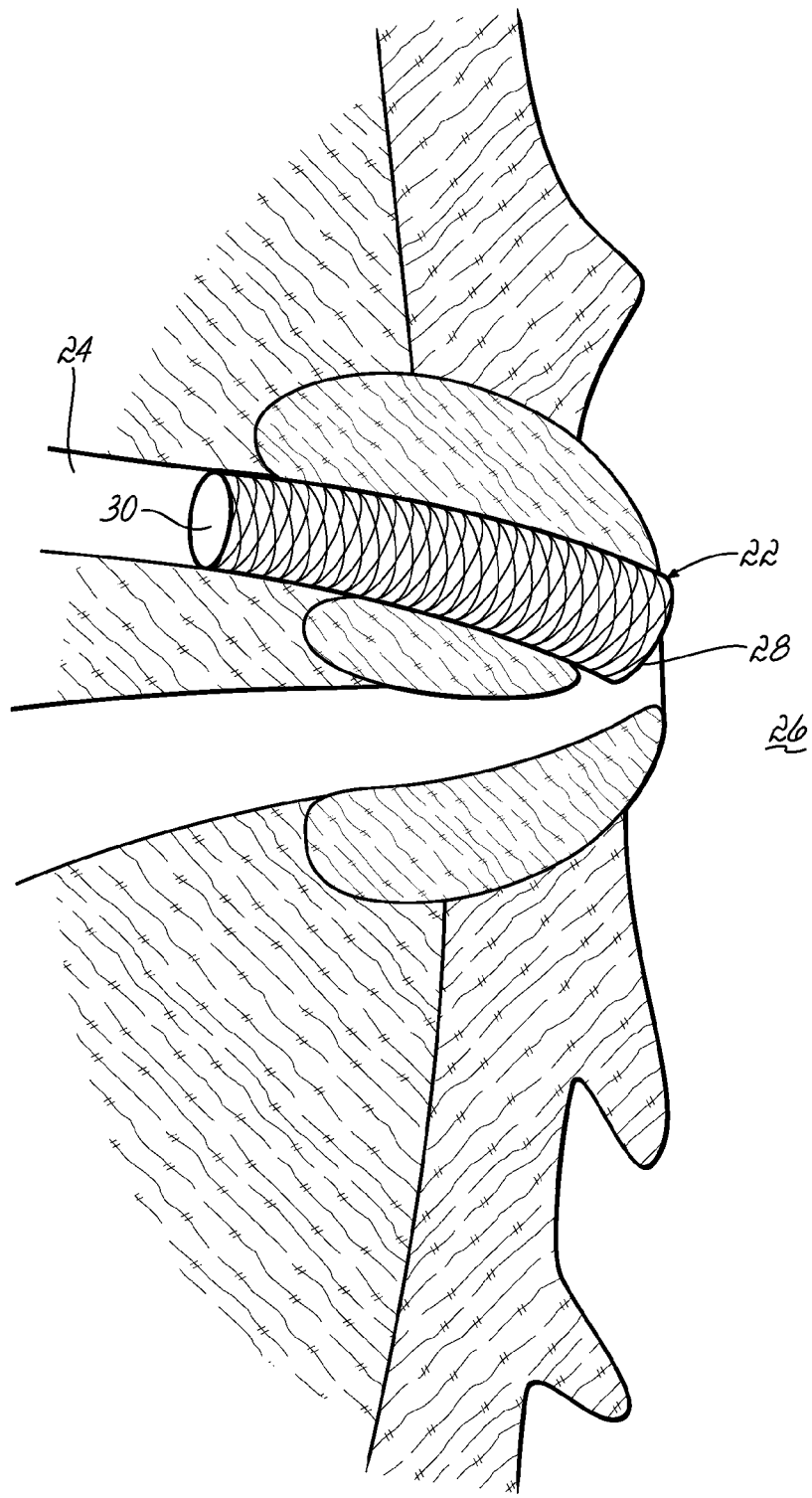
FIG. 4 is an exemplary biliary stent positioned at the intersection of the biliary duct and the duodenum.

The present invention is optimally used to form a stent to treat ductal obstruction and occlusion in the biliary stent in the treatment of cholangiocarcinoma. As shown in FIG. 4, the stent 22 with increased dendrites can be inserted into the biliary duct 24, particularly at the locus where the biliary duct 24 enters the duodenum 26. The particular stent 22 shown in FIG. 4 has an enlarged proximal end 28 toward the duodenum 26 and a narrower distal end 30 in the biliary duct, which promotes fluid flow into the duodenum.

Such a design would typically not be preferred, since it would encourage the dislocation of the stent into the duodenum. However, due to the formation of the dendrites on the surface of the stent 22, the stent 22 is more likely to remain in place.

The stent is inserted using standard techniques. It can be an expandable stent, or can be preformed to the desired size and introduced endoscopically. This stent structure provides unique benefits in the treatment of cholangiocarcinoma. The tin-117 m being a CEES omitting radioisotope provides precise dosage of radiation within a precise location. However, the dendrites enhance this by extending outwardly from the stent surface toward the duct, thus increasing the distance that the radiation travels relative to the stent. This also makes the radiation emission somewhat more random, which, due to the nature of cancer, enhances the treatment. Further, the radiation will inhibit bacterial and fungal growth within the duct, deterring blockage.

In a further improvement of the present invention, the electroplated implant can be further coated with a thin, less than 50 micron, coating of type 1 and/or type 2 collagen, which will act to induce hemostasis. As shown in FIG. 3, coating 20 can be a thin layer of type 1 and type 2 collagen.

Although the above example is explicit with respect to a stent, and particularly an expandable biliary stent, any implant, particularly any radioactive implant, where movement of the implant presents an issue, can take advantage of the present invention. Electroplating the implant with a metallic surface with enhanced dendrite formation, will improve the contact between the surface and a surface of that body to inhibit movement.

Further, with respect to any radioactive implant, whether movement is an issue or not, formation of a radioactive metallic surface with increased dendrite formation will improve radiation emission from the implant. The dendrite formation not only increases the distance from the implant that the radiation is emitted, it also provides increased surface area that is radioactive thereby increasing the emissions. The present invention can be used with implants that are expandable or of a fixed size, rigid or flexible; basically any implant that can be electroplated with a biologically acceptable metal.

This has been a description of the present invention along with the preferred method of practicing the present invention.

However, the invention itself should only be defined by the appended claims, wherein I claim:

1. A method of treating cholangiocarcinoma comprising implanting a self-supporting tubular member into a bile duct of a patient wherein said member has an exterior surface and an interior surface said exterior surface comprising a metal film electroplated onto said member wherein said metal film has an exterior surface comprising greater than 1.5 percent by area dendrites;
   wherein said metal film comprises tin-117m;
   and wherein said member has a proximal end nearer a duodenum of said patient and a distal end wherein said proximal end is larger than said distal end.

2. The method claimed in claim 1 wherein said member is a stent.

3. The method claimed in claim 1 wherein said surface comprises at least 12 percent by area dendrites.

4. A radioactive implant said implant having an electroplated metal exterior surface wherein said exterior surface is at least about 1.7% dendrites, wherein said metal comprises tin-117m.

5. The radioactive implant claimed in claim 4 wherein said surface is at least about 3% dendrites.

6. The radioactive implant claimed in claim 4 wherein said surface is at least about 5% dendrites.

7. The radioactive implant claimed in claim 4 wherein said implant comprises at least about 12% dendrites.

8. The radioactive implant claimed in claim 4 wherein said surface is further coated with collagen.

9. The implant claimed in claim 4 wherein said implant is tubular.

10. The implant claimed in claim 9 wherein said implant is a stent.

11. An implant comprising an expandable stent having an exterior metal surface comprising an electroplated metal film wherein said exterior surface is at least about 1.7 percent dendrites by area, wherein said metal is tin-117m.

12. The method of treating pancreatic cancer by implanting the stent of claim 11 in one of a common bile duct, a pancreatic duct or a hilar bile duct.

* * * * *